(12) United States Patent
Imamura et al.

(10) Patent No.: US 12,059,286 B2
(45) Date of Patent: Aug. 13, 2024

(54) RADIOGRAPHY APPARATUS

(71) Applicant: FUJIFILM Corporation, Tokyo (JP)

(72) Inventors: Ryo Imamura, Kanagawa (JP); Masayoshi Matsuura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 518 days.

(21) Appl. No.: 17/214,486

(22) Filed: Mar. 26, 2021

(65) Prior Publication Data

US 2021/0212653 A1    Jul. 15, 2021

Related U.S. Application Data

(63) Continuation of application No. PCT/JP2019/037929, filed on Sep. 26, 2019.

(30) Foreign Application Priority Data

Sep. 27, 2018    (JP) .................................. 2018-183000

(51) Int. Cl.
*H05G 1/10* (2006.01)
*A61B 6/00* (2006.01)
*H05G 1/32* (2006.01)

(52) U.S. Cl.
CPC ................ *A61B 6/56* (2013.01); *H05G 1/10* (2013.01); *H05G 1/32* (2013.01); *A61B 6/4441* (2013.01)

(58) Field of Classification Search
None
See application file for complete search history.

(56) References Cited

U.S. PATENT DOCUMENTS

| | | | | |
|---|---|---|---|---|
| 5,539,798 A * | 7/1996 | Asahina | ................. | A61B 6/488 378/98.7 |
| 5,867,553 A | 2/1999 | Gordon et al. | | |
| 6,502,984 B2 * | 1/2003 | Ogura | .................... | A61B 6/544 378/63 |
| 7,638,773 B2 * | 12/2009 | Kuwabara | .............. | G03B 42/04 250/370.08 |

(Continued)

FOREIGN PATENT DOCUMENTS

| | | |
|---|---|---|
| JP | S64-030429 A | 2/1989 |
| JP | H06-208899 A | 7/1994 |

(Continued)

OTHER PUBLICATIONS

MachineTranslation of JP 2014093159 (Year: 2014).*

(Continued)

*Primary Examiner* — Marcus H Taningco
*Assistant Examiner* — Djura Malevic
(74) *Attorney, Agent, or Firm* — Studebaker & Brackett PC

(57) ABSTRACT

A radiography apparatus includes a drive circuit that drives a radiation source, an internal power supply that makes a current flow to the drive circuit at a first voltage, an external power supply that makes a current flow to the drive circuit at a second voltage different from the first voltage, a power feed controller that performs power feed to the drive circuit using at least one of the internal power supply or the external power supply, and a radiation output restriction unit that controls an output of radiation by a power supply to be used in the power feed to the drive circuit by the power feed controller.

12 Claims, 8 Drawing Sheets

(56) References Cited

U.S. PATENT DOCUMENTS

| | | | | |
|---|---|---|---|---|
| 7,720,198 B2* | 5/2010 | Schliermann | A61B 6/08 378/108 |
| 7,726,879 B2* | 6/2010 | Abe | A61B 6/08 378/94 |
| 7,737,427 B2* | 6/2010 | Kito | A61B 6/588 250/580 |
| 7,935,932 B2* | 5/2011 | Kito | G03B 42/04 250/580 |
| 8,199,876 B2* | 6/2012 | Graumann | A61B 6/4441 378/63 |
| 8,227,757 B2* | 7/2012 | Yokoyama | A61B 6/542 250/354.1 |
| 8,237,127 B2* | 8/2012 | Yoshida | G03B 42/04 378/182 |
| 8,351,568 B2* | 1/2013 | Minnigh | A61B 6/5241 378/204 |
| 8,553,839 B2* | 10/2013 | Hendriks | A61B 6/4441 378/63 |
| 8,767,919 B2* | 7/2014 | Nishino | A61B 6/4007 378/62 |
| 8,827,554 B2* | 9/2014 | Lalena | A61B 6/547 378/98.5 |
| 8,867,702 B2* | 10/2014 | Nishino | A61B 6/4283 378/92 |
| 8,873,708 B2* | 10/2014 | Sugiyama | A61B 6/504 378/151 |
| 9,028,144 B2* | 5/2015 | Choi | A61B 6/54 378/208 |
| 9,149,247 B2* | 10/2015 | Lee | A61B 6/4452 |
| 9,241,682 B2* | 1/2016 | Aram | A61B 6/505 |
| 9,462,985 B2* | 10/2016 | Hu | A61B 6/545 |
| 9,799,114 B2* | 10/2017 | Piron | G09B 23/30 |
| 9,931,089 B2* | 4/2018 | Nariyuki | A61B 6/107 |
| 9,936,879 B2* | 4/2018 | Piron | A61B 34/30 |
| 9,955,927 B2* | 5/2018 | Hendriks | A61B 6/4441 |
| 9,968,502 B2* | 5/2018 | Hight | A61B 6/0492 |
| 9,974,504 B2* | 5/2018 | Lee | A61B 6/469 |
| 10,004,465 B2* | 6/2018 | Krauss | A61B 6/544 |
| 10,034,649 B2* | 7/2018 | Kim | A61B 6/544 |
| 10,039,509 B2* | 8/2018 | Okusu | A61B 6/0407 |
| 10,045,751 B2* | 8/2018 | Okusu | A61B 6/0407 |
| 10,098,598 B2* | 10/2018 | Lee | A61B 6/469 |
| 10,143,428 B2* | 12/2018 | Eun | A61B 6/461 |
| 10,172,574 B2* | 1/2019 | Schäfer | A61B 6/0492 |
| 10,181,074 B2* | 1/2019 | Braun | G06F 18/40 |
| 10,188,365 B2* | 1/2019 | Lee | A61B 6/544 |
| 10,194,882 B2* | 2/2019 | Kwak | A61B 6/10 |
| 10,285,656 B2* | 5/2019 | Wang | A61B 6/461 |
| 10,376,217 B2* | 8/2019 | Schmidt | A61B 5/055 |
| 10,709,406 B2* | 7/2020 | Aoshima | A61B 6/589 |
| 10,813,617 B2* | 10/2020 | Inoue | A61B 6/461 |
| 10,856,821 B2* | 12/2020 | Onobori | A61B 6/44 |
| 10,939,884 B2* | 3/2021 | Nariyuki | A61B 6/462 |
| 11,207,038 B2* | 12/2021 | Sutter | A61B 5/0035 |
| 11,382,579 B2* | 7/2022 | Shimizukawa | A61B 6/461 |
| 11,399,796 B2* | 8/2022 | Umekawa | A61B 6/42 |
| 11,571,178 B2* | 2/2023 | Kimura | G06V 40/10 |
| 2006/0109958 A1* | 5/2006 | Ertel | A61B 6/547 378/205 |
| 2008/0002028 A1* | 1/2008 | Miyata | H04N 23/00 348/169 |
| 2009/0136000 A1* | 5/2009 | Nishii | A61B 6/08 378/98.3 |
| 2009/0232273 A1* | 9/2009 | Sendai | A61B 5/0091 378/20 |
| 2011/0049370 A1* | 3/2011 | Yoshida | A61B 6/548 250/354.1 |
| 2011/0073767 A1* | 3/2011 | Iwakiri | G03B 42/02 250/370.08 |
| 2011/0110497 A1* | 5/2011 | Nishino | A61B 6/4283 378/116 |
| 2013/0114793 A1* | 5/2013 | Ohta | A61B 6/588 378/63 |
| 2013/0142309 A1 | 6/2013 | Iwakiri et al. | |
| 2013/0200842 A1* | 8/2013 | Takahashi | A61B 6/548 320/108 |
| 2013/0223596 A1 | 8/2013 | Kojima et al. | |
| 2013/0272502 A1* | 10/2013 | Watanabe | H05G 1/26 378/98 |
| 2014/0064447 A1* | 3/2014 | Ogura | A61B 6/40 378/140 |
| 2014/0201439 A1* | 7/2014 | Sasaki | G06F 11/1092 711/114 |
| 2014/0241500 A1* | 8/2014 | Yasuda | A61B 6/08 600/436 |
| 2015/0055753 A1* | 2/2015 | Tajima | A61B 6/4283 378/62 |
| 2015/0228071 A1* | 8/2015 | Jockel | H04N 13/204 382/132 |
| 2018/0116524 A1* | 5/2018 | Aoshima | A61B 6/4452 |
| 2018/0116623 A1* | 5/2018 | Inoue | A61B 6/547 |
| 2018/0367751 A1* | 12/2018 | Devendran | H04N 5/57 |

FOREIGN PATENT DOCUMENTS

| | | |
|---|---|---|
| JP | H11-500340 A | 1/1999 |
| JP | 2009-237230 A | 10/2009 |
| JP | WO2012/544288 A1 | 5/2012 |
| JP | 2012-129087 A | 7/2012 |
| JP | 2014-093159 A | 5/2014 |
| JP | 2014-200436 A | 10/2014 |
| JP | 2016-111772 A | 6/2016 |
| WO | 2012/026518 A1 | 3/2012 |
| WO | WO-2017187579 A1 * | 11/2017 ............ A61B 6/00 |

OTHER PUBLICATIONS

International Search Report issued in PCT/JP2019/037929 ; mailed Dec. 24, 2019.

Written Opinion issued in PCT/JP2019/037929; mailed Dec. 24, 2019.

An Office Action; "Notice of Reasons for Refusal", mailed by the Japanese Patent Office on Apr. 12, 2022, which corresponds to Japanese Patent Application No. 2020-549373 and is related to U.S. Appl. No. 17/214,486; with English language translation.

An Office Action mailed by China National Intellectual Property Administration on Nov. 7, 2023, which Corresponds to Chinese Patent Application No. 201980063852.6 and is related to U.S. Appl. No. 17/214,486; with English language translation.

* cited by examiner

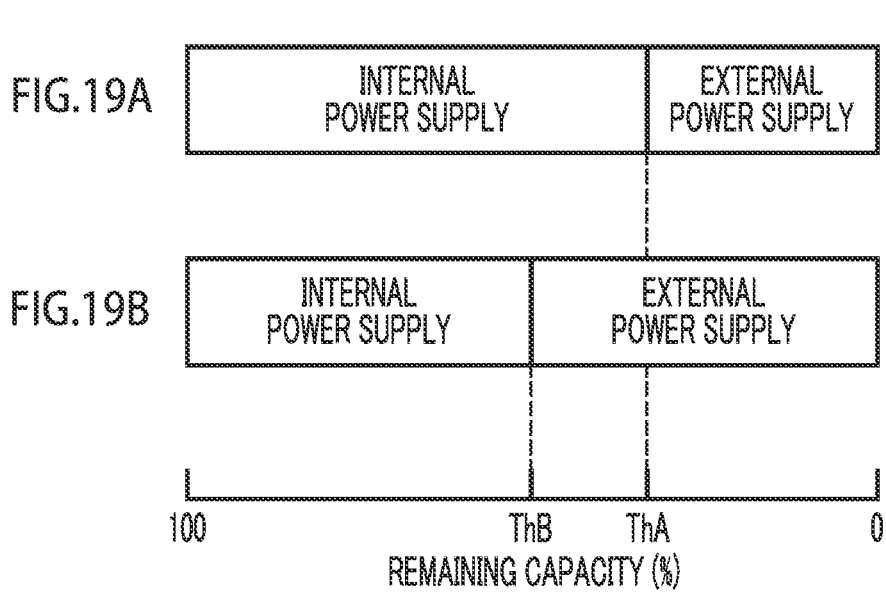
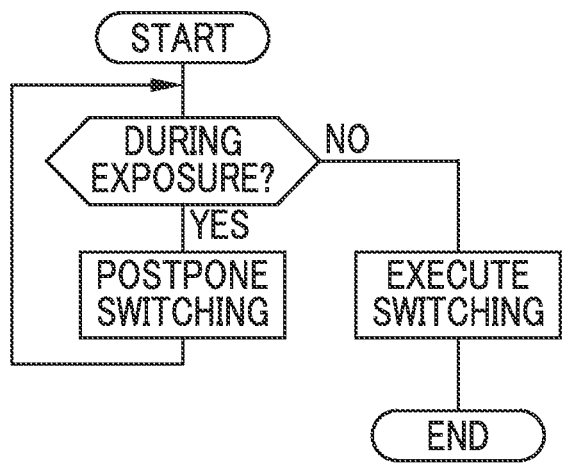
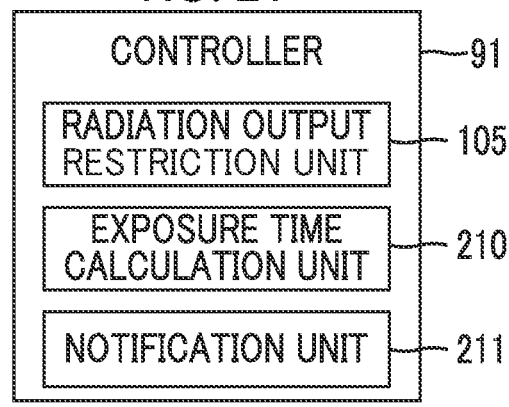

RADIOGRAPHY APPARATUS

CROSS-REFERENCE TO RELATED APPLICATIONS

This application is a Continuation of PCT International Application No. PCT/JP2019/037929 filed on 26 Sep. 2019, which claims priority under 35 U.S.C § 119(a) to Japanese Patent Application No. 2018-183000 filed on 27 Sep. 2018. The above application is hereby expressly incorporated by reference, in its entirety, into the present application.

BACKGROUND OF THE INVENTION

1. Field of the Invention

The present invention relates to a radiography apparatus that generates radiation for radiography or the like.

2. Description of the Related Art

A radiography apparatus that images a subject using radiation has become widespread. The radiography apparatus comprises a radiation generation unit that generates radiation, and a radiation detection panel that obtains a radiographic image of a subject by detecting the radiation. For example, an X-ray imaging apparatus that images a subject using X-rays is known. The X-ray imaging apparatus comprises an X-ray generation device that generates X-rays, and an X-ray detection device that obtains an X-ray image of a subject.

Among recent radiography apparatuses, a mobile radiography apparatus that moves to any place, such as a patient's room where a patient is present, and performs radiography is known. The mobile radiography apparatus comprises an internal power supply, such as a battery or a capacitor in which electric power is stored.

For example, an X-ray image diagnostic apparatus of JP2014-200436A supplies electric power to an X-ray source through an exposure battery. Then, the X-ray image diagnostic apparatus of JP2014-200436A switches the on and off of power feed from an external power supply to the exposure battery according to a remaining capacity or the like of the exposure battery.

Furthermore, a mobile X-ray apparatus of JP2012-544288A (corresponding to US2013/0223596A1) supplies electric power to an X-ray generation unit through a battery. Then, the mobile X-ray apparatus of JP2012-544288A has an operation mode in which electric power is also supplied from the battery to units other than the X-ray generation unit in a case where a rapid voltage drop or the like occurs in a commercial alternating current power supply in an operation mode in which electric power is supplied from a commercial alternating current power supply to units other than the X-ray generation unit.

A stationary CT scanner may also be mounted with a battery, and electric power may be supplied from the battery to the scanner in a case where an external power supply does not meet electric power demand (JP1999-500340A (JP-H11-500340A, corresponding to U.S. Pat. No. 5,867,553A)).

SUMMARY OF THE INVENTION

The radiation generation unit may consume electric power not covered by a general commercial power supply. For example, while the capacity of the general commercial power supply in Japan is 1500 W, in X-ray imaging, electric power (for example, 2000 W) exceeding 1500 W may be required to generate X-rays. For this reason, in the radiation generation unit that consumes electric power exceeding the capacity of the external power supply, an internal power supply that covers the above-described electric power supplies electric power to the radiation generation unit.

Note that the radiation generation unit that receives the supply of electric power from the internal power supply may not be operated due to an insufficient remaining capacity, deterioration, or the like of the internal power supply, and as a result, radiography may not be performed. Furthermore, even though an external power supply that charges the internal power supply is provided, in a case where the supply of electric power to the radiation generation unit is performed through the internal power supply, the external power supply may not be operated due to an insufficient remaining capacity of the internal power supply, deterioration of the internal power supply, or the like, and radiography may not be performed.

Even though the radiography apparatus is prepared, in a case where some radiography cannot be performed for the above-described reason, burden is imposed on a physician, a patient, or the like.

Accordingly, an object of the invention is to provide a radiography apparatus that uses an external power supply and enables generation of radiation with a restricted output even in a radiography apparatus that operates with supply of electric power from an internal power supply.

A radiography apparatus of the invention comprises a radiation source that generates radiation, a drive circuit that drives the radiation source, an internal power supply that makes a current flow to the drive circuit at a first voltage, an external power supply that makes a current flow to the drive circuit at a second voltage different from the first voltage, a power feed controller that performs power feed to the drive circuit using at least one of the internal power supply or the external power supply, and a radiation output restriction unit that controls an output of the radiation by a power supply to be used in the power feed to the drive circuit by the power feed controller.

It is preferable that the power feed controller performs the power feed to the drive circuit using the internal power supply and the external power supply.

It is preferable that the power feed controller performs the power feed to the drive circuit using the internal power supply and the external power supply in a case where the first voltage is smaller than the second voltage.

It is preferable that the radiation output restriction unit restricts the output of the radiation using a characteristic of the internal power supply.

It is preferable that the radiation output restriction unit restricts the output of the radiation using a remaining capacity of the internal power supply.

It is preferable that the radiation output restriction unit restricts the output of the radiation using internal resistance of the internal power supply.

It is preferable that the radiation output restriction unit restricts the output of the radiation by restricting the current flowing from the external power supply to the drive circuit.

It is preferable that the radiation output restriction unit restricts the output of the radiation by restricting a range in which setting of the output of the radiation is possible.

It is preferable that the power feed controller switches a power supply, which performs the power feed to the drive circuit, between the internal power supply and the external power supply.

It is preferable that the power feed controller performs switching between the internal power supply and the external power supply using a threshold value set for a remaining capacity of the internal power supply.

It is preferable that the power feed controller sets the threshold value that is different between a case where a static image is captured using the radiation and a case where video is captured using the radiation.

It is preferable that the threshold value that is set in a case where the video is captured using the radiation is greater than the threshold value that is set in a case where the static image is captured using the radiation.

It is preferable that the power feed controller uses the threshold value having different values between a case of switching from the internal power supply to the external power supply and a case of switching from the external power supply to the internal power supply.

It is preferable that the power feed controller postpones the switching of the power supply while the radiation is being generated.

It is preferable that the radiography apparatus further comprises a notification unit that notifies of a time for which the power feed to the drive circuit using the internal power supply is possible.

It is preferable that the radiation output restriction unit restricts the output of the radiation in a case where the power feed controller performs switching from the internal power supply to the external power supply.

With the radiography apparatus of the invention, even in a radiography apparatus that operates with supply of electric power from an internal power supply, it is possible to generate radiation with a restricted output using an external power supply. As a result, even though the internal power supply undergoes an insufficient remaining capacity, deterioration, or the like, it is possible to perform some radiography using the radiography apparatus.

BRIEF DESCRIPTION OF THE DRAWINGS

FIGS. 19A and 19B are explanatory views showing a relationship between a threshold value in a case of switching from the internal power supply to the external power supply and a threshold value in a case of switching from the external power supply to the internal power supply.

FIG. 20 is a flowchart of performing switching of a power supply.

FIG. 21 is a block diagram of a controller.

DESCRIPTION OF THE PREFERRED EMBODIMENTS

First Embodiment

Figure 1:
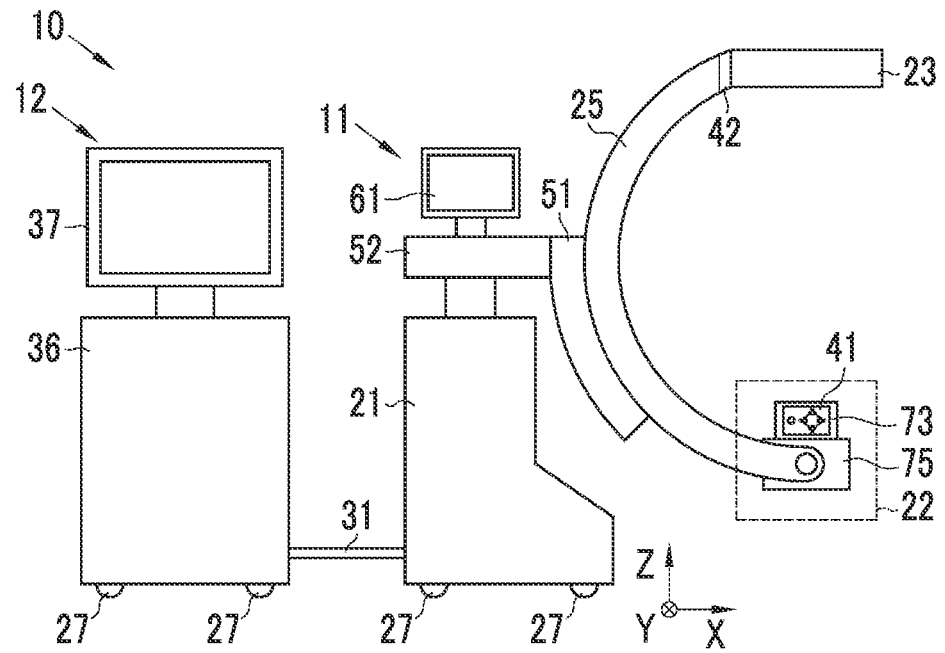
FIG. 1 is a schematic view of a radiography apparatus.

As shown in FIG. 1, a radiography apparatus 10 comprises an imaging unit 11 and a display unit 12. The imaging unit 11 is a unit that generates radiation and images a subject 15 (see FIG. 4) using the radiation. The display unit 12 is a unit that displays or the like a radiographic image captured using the imaging unit 11.

The imaging unit 11 comprises an imaging unit body 21, a radiation generation unit 22, a radiography unit 23, and a C-arm 25.

The imaging unit body 21 integrally controls the operations of the radiation generation unit 22, the radiography unit 23, the C-arm 25, and the like. The imaging unit body 21 is connected to the display unit 12 in a wired or wireless manner. In the embodiment, the imaging unit body 21 is connected to the display unit 12 using a cable 31 in a wired manner. With this, the imaging unit 11 supplies a radiographic image, electric power, and the like to the display unit 12. The display unit 12 comprises a display unit body 36, and a monitor 37 that displays a radiographic image or the like. A caster 27 is attached to the imaging unit body 21 and the display unit body 36. For this reason, the radiography apparatus 10 is movable, and can perform radiography in a patient's room where a patient who is the subject 15 is present.

The radiation generation unit 22 generates radiation in a case of performing radiography. The radiation generation unit 22 is rotationally movably attached to one end of the C-arm 25. In the embodiment, the rotational movement of the radiation generation unit 22 is possible within a plane of the C-arm 25. For example, in a case where the C-arm 25 is disposed within an XZ plane (see FIG. 1), the radiation generation unit 22 can be rotationally moved in an XZ in-plane direction. Furthermore, the radiation generation unit 22 comprises a first operating unit 41. The first operating unit 41 is an operating unit that is provided to operate the radiation generation unit 22, and may be validated or invalidated according to the usages of the radiography apparatus 10. In the embodiment, although the radiation that is generated in the radiation generation unit 22 is X-rays, the radiation generation unit 22 can be substituted with a configuration of generating radiation other than X-rays.

The radiography unit 23 is attachably and detachably to the other end (an end portion opposite to the end portion to which the radiation generation unit 22 is attached) of the C-arm 25. The radiography unit 23 images the subject 15 using the radiation generated by the radiation generation unit 22. The attachment and detachment detection unit 42 is a mechanism that detects attachment and detachment of the radiography unit 23, and is, for example, a switch mechanism that is turned on in a case where the radiography unit 23 is attached. The attachment and detachment detection unit 42 is incorporated in the end portion of the C-arm 25 attached to the radiography unit 23 in the embodiment. The attachment and detachment of the radiography unit 23 includes attachment and detachment of a part of components of the radiography unit 23.

In principle, the C-arm 25 is held at a position (hereinafter, referred to as a confronting position) where the radiation generation unit 22 confronts the radiography unit 23. Specifically, the C-arm 25 holds the radiation generation unit 22 and the radiography unit 23 at the confronting position in a case where both the radiation generation unit 22 and the radiography unit 23 are attached. Note that the radiography apparatus 10 can detach the radiography unit 23 from the C-arm 25 to perform radiography. Accordingly, in a case where the radiography unit 23 is detached from the C-arm 25 to perform radiography, the C-arm 25 holds the radiation generation unit 22 at any position and in any orientation (normally, a position confronting the radiography unit 23). The confronting position is a position where the radiography unit 23 can capture the radiation generated by the radiation generation unit 22 substantially vertically. The term "substantially vertically" allows an inclination or the like of at least one of the radiation generation unit 22 or the radiography unit 23 without causing trouble in imaging of the subject 15.

The C-arm 25 is connected to a lifting mechanism 52 through a sliding mechanism 51. The sliding mechanism 51 holds the C-arm 25 in a slidable (slidingly movable) manner in an arc shape. As the C-arm 25 is slid by the sliding mechanism 51, the radiation generation unit 22 and the radiography unit 23 can be rotated around the center (the center of a "C" shape that is an arc) of the C-arm 25 while maintaining the confronting position. For example, in a case where the radiation generation unit 22 and the radiography unit 23 are disposed within the XZ plane as shown in FIG. 1, as the C-arm 25 is slid using the sliding mechanism 51, the C-arm 25, and the radiation generation unit 22 and the radiography unit 23 attached to the C-arm 25 can be rotated around the Y-axis.

The sliding mechanism 51 is rotatably attached to the lifting mechanism 52 liftably attached to the imaging unit body 21 in a vertical direction (Z-axis direction). For this reason, the C-arm 25 is rotatable around a specific direction (X-axis) within a horizontal plane. As the lifting mechanism 52 is lifted up and down, the C-arm 25, and the radiation generation unit 22 and the radiography unit 23 attached to the C-arm 25 can be optionally moved vertically upward (Z-axis positive direction) or vertically downward (Z-axis negative direction).

In addition to the above-described configuration, the imaging unit body 21 comprises a second operating unit 61. The second operating unit 61 is an operating unit that operates the respective units of the imaging unit body 21 including the radiation generation unit 22. An operation using the second operating unit 61 can be performed at any timing.

Figure 2:
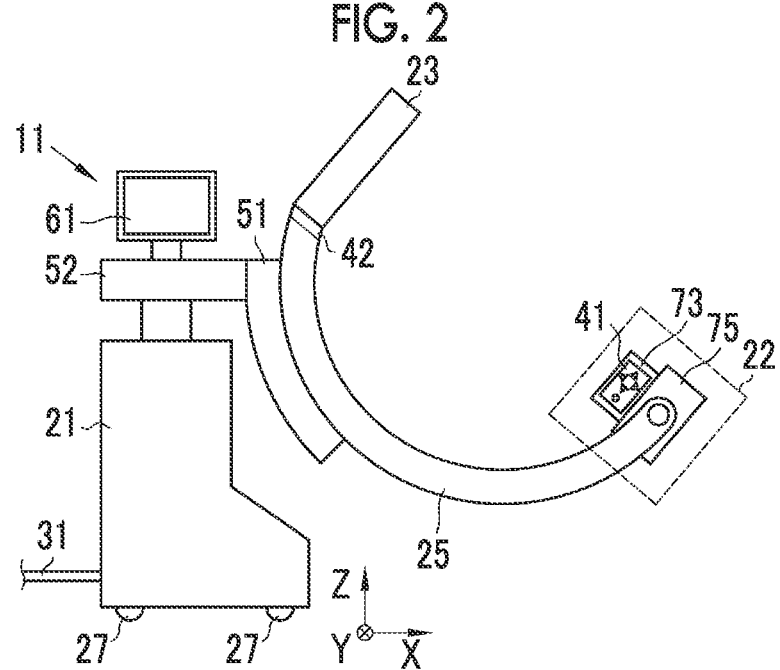
FIG. 2 shows the radiography apparatus in which a C-arm is slid.
Figure 3:
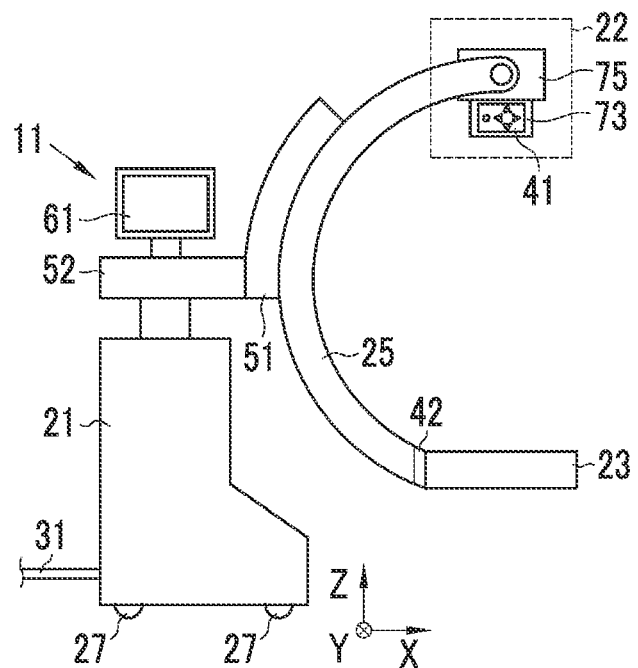
FIG. 3 shows the radiography apparatus in which the C-arm is rotated.
Figure 4:
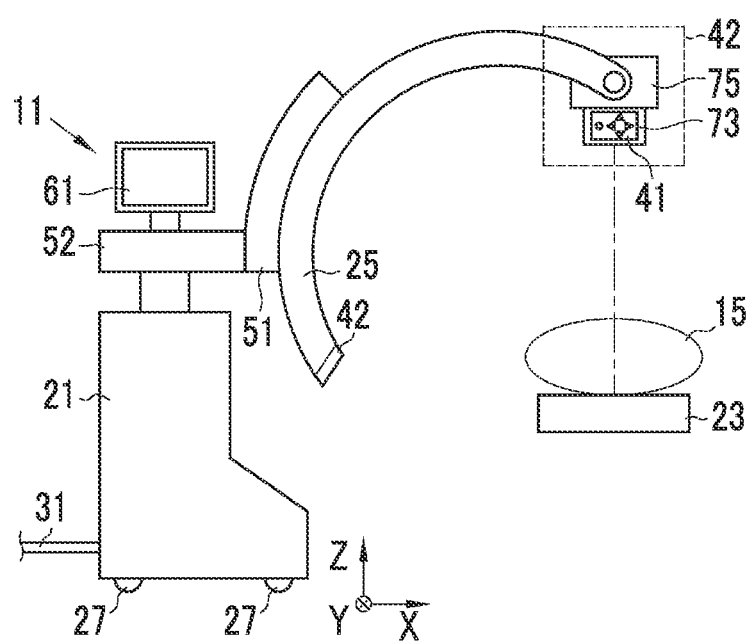
FIG. 4 is a schematic view in a case where a radiography panel is separated to perform imaging.

The radiography apparatus 10 configured as described above can image the subject 15 in a form of a static image or video using radiation. That is, the radiography apparatus 10 has a static image capturing mode in which a static image of the subject 15 is captured using radiation, and a video capturing mode in which video of the subject 15 is captured using radiation. In the embodiment, as shown in FIGS. 1 and 2, capturing of video is performed by disposing the radiation generation unit 22 substantially vertically downward (Z-axis negative direction) relatively to the radiography unit 23 and disposing the radiography unit 23 substantially vertically upward (Z-axis positive direction) relatively to the radiation generation unit 22. On the other hand, as shown in FIGS. 3 and 4, capturing of a static image is performed by disposing the radiation generation unit 22 substantially vertically upward relatively to the radiography unit 23. Furthermore, as shown in FIG. 4, capturing of a static image can be performed in a state in which the radiography unit 23 is detached from the C-arm 25. In this case, the radiography unit 23 is disposed behind the subject 15 (in FIG. 4, on a Z-direction negative side of the subject 15) as viewed from the radiation generation unit 22.

Figure 5:
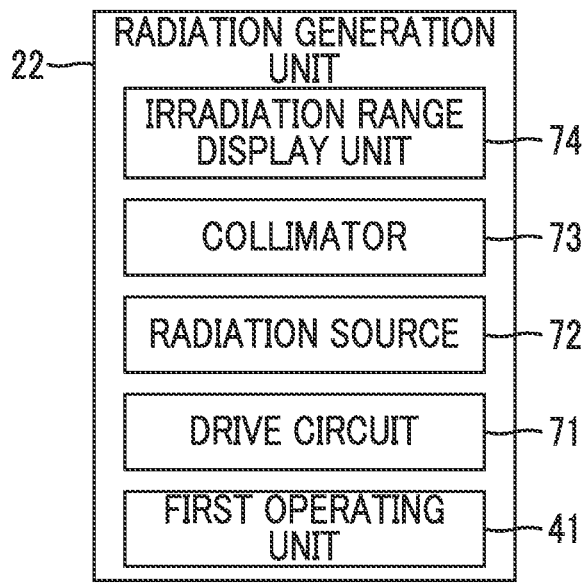
FIG. 5 is a block diagram of a radiation generation unit.

As shown in FIG. 5, the radiation generation unit 22 comprises a drive circuit 71, a radiation source 72, the collimator 73, an irradiation range display unit 74, and the first operating unit 41.

The drive circuit 71 is a drive circuit that drives the radiation source 72, and is a so-called high-voltage generation circuit. The drive circuit 71 supplies electric power needed to generate radiation to the radiation source 72. A high voltage in the drive circuit 71 refers to a voltage needed for the radiation source 72 to generate radiation.

The radiation source 72 receives supply of needed electric power from the drive circuit 71 to generate radiation. In the embodiment, the radiation source 72 is an X-ray source that generates X-rays. In the embodiment, the radiation source 72 is integrated with the drive circuit 71, and constitutes a so-called mono-tank 75 (see FIG. 1).

The collimator 73 is a mechanism that adjusts an irradiation range of the radiation generated by the radiation source 72. In the radiography apparatus 10, the irradiation range of the radiation can be appropriately changed according to conditions or the like of imaging using the collimator 73. The collimator 73 is disposed in a direction (the radiography unit 23 side) in which the radiation source 72 (mono-tank 75) emits the radiation.

The irradiation range display unit 74 is a light emitting element, such as a light emitting diode or a lamp, and irradiates the subject 15 with visible light from the vicinity of substantially a generation point (so-called focus) of X-rays through the collimator 73. With this, the irradiation range of the radiation is displayed on the subject 15.

The first operating unit 41 is a controller that is provided to control the respective units of the radiation generation unit 22. Specifically, the first operating unit 41 is an operating unit of the collimator 73 and the irradiation range display unit 74. Accordingly, a physician or the like who is a user can adjust the irradiation range of the radiation by operating the first operating unit 41. Furthermore, the physician or the like can turn on or off the display of the irradiation range of the radiation by operating the first operating unit 41. The first operating unit 41 is provided in, for example, the collimator 73 (see FIG. 1 or the like).

Figure 6:
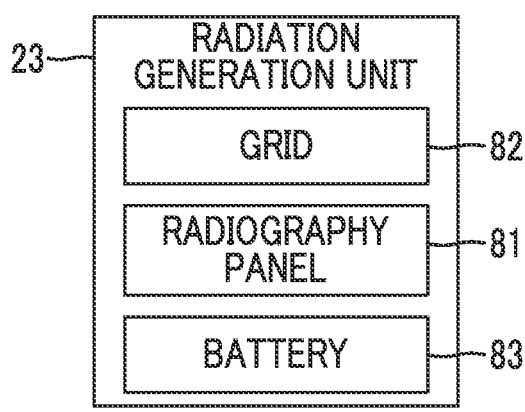
FIG. 6 is a block diagram of a radiography unit.

As shown in FIG. 6, the radiography unit 23 comprises a radiography panel 81, a grid 82, a battery 83, and the like.

The radiography panel 81 receives the radiation generated by the radiation generation unit 22 to image the subject 15. That is, the radiography panel 81 (or the entire radiography unit 23) is a so-called direct conversion type or indirect conversion type flat panel detector (FPD). In the embodiment, the radiography panel 81 included in the radiography unit 23 can be replaced with another radiography panel that is different in panel size or the like.

The grid 82 is a member that improves resolution or the like of a radiographic image by eliminating scattered rays, and is disposed on an incidence side (a side on which the radiation generation unit 22 is present) of the radiation of the radiography panel 81. The grid 82 can be replaced. The replacement of the grid 82 can be performed along with the radiography panel 81 or separately from the radiography panel 81. The grid 82 can be included in the radiography panel 81.

The battery 83 is a power supply that supplies electric power to the radiography panel 81. The battery 83 can be included in the radiography panel 81. In the embodiment, since the radiography unit 23 can be detached from the C-arm 25 and used, the radiography unit 23 is mounted with the battery 83. Meanwhile, in the radiography apparatus 10, a radiography panel that is attached to the C-arm 25 and receives supply of electric power from the imaging unit body 21 to perform radiography can also be used. In this case, the radiography unit 23 can omit the battery 83.

Figure 7:
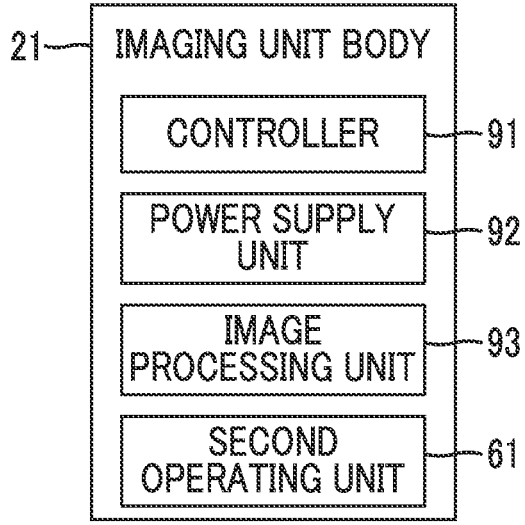
FIG. 7 is a block diagram of an imaging unit body.

As shown in FIG. 7, the imaging unit body 21 comprises, in addition to the second operating unit 61, a controller 91 that integrally controls the operations of the respective units of the radiography apparatus 10, a power supply unit 92 that supplies electric power to the respective units of the radiography apparatus 10, and an image processing unit 93 that executes image processing on a radiographic image captured using the radiography unit 23 as needed. In the embodiment, although the imaging unit body 21 comprises the image processing unit 93, the image processing unit 93 can be provided in the display unit body 36.

Figure 8:
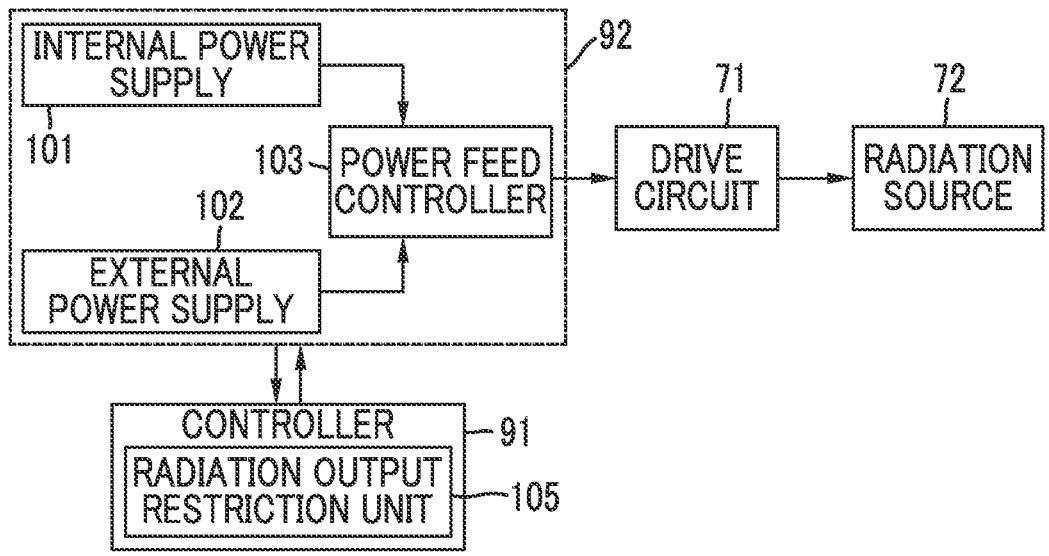
FIG. 8 is a block diagram showing the configuration of a power supply unit.

As shown in FIG. 8, the power supply unit 92 comprises an internal power supply 101, an external power supply 102, and a power feed controller 103. Furthermore, the controller 91 comprises a radiation output restriction unit 105.

The internal power supply 101 is a power supply that stores electric power inside the radiography apparatus 10, and is, for example, a battery or a capacitor. In the embodiment, the internal power supply 101 is a battery. The internal power supply 101 supplies electric power to not only the controller 91 and the like but also the drive circuit 71 through the power feed controller 103. In a case where the internal power supply 101 supplies electric power to the drive circuit 71, the internal power supply 101 makes a current flow to the drive circuit 71 at a first voltage. The internal power supply 101 is detached from the power supply unit 92 and stores electric power. Note that the internal power supply 101 can receive supply of electric power from the external power supply 102 to store electric power. For example, in a case where the internal power supply 101 is constituted of a capacitor, electric power is stored in the internal power supply 101 using the external power supply 102.

The external power supply 102 is a power supply that acquires electric power from the outside of the radiography apparatus 10, and is, for example, a circuit or the like (so-called alternating current (AC)/direct current (DC) power supply) that obtains electric power from a commercial alternating current power supply (electrical outlet) provided in a patient's room or the like. The external power supply 102 makes a current flow to the drive circuit 71 at a second voltage different from the first voltage.

Since the internal power supply 101 is a battery or the like, there is a case where a voltage (first voltage) that is output from the internal power supply 101 changes with a remaining capacity, an increase in internal resistance due to deterioration over time, power consumption of the drive circuit 71, or the like. For this reason, in comparing (distinguishing) the internal power supply 101 and the external power supply 102, the "first voltage" refers to an initial voltage (initial electromotive force) of the internal power supply 101 without taking into consideration such change. In other cases, the "first voltage" refers to a voltage that is actually output from the internal power supply 101. In the embodiment, the initial voltage (initial electromotive force) of the internal power supply 101 is higher than the second voltage that is output from the external power supply 102. The voltage (second voltage) that is output from the external power supply 102 to the drive circuit 71 is constant.

The power feed controller 103 performs power feed to the drive circuit 71 using at least one of the internal power supply 101 or the external power supply 102. In the embodiment, the power feed controller 103 performs the power feed to the drive circuit 71 using both the internal power supply 101 and the external power supply 102 as needed.

Figure 9:
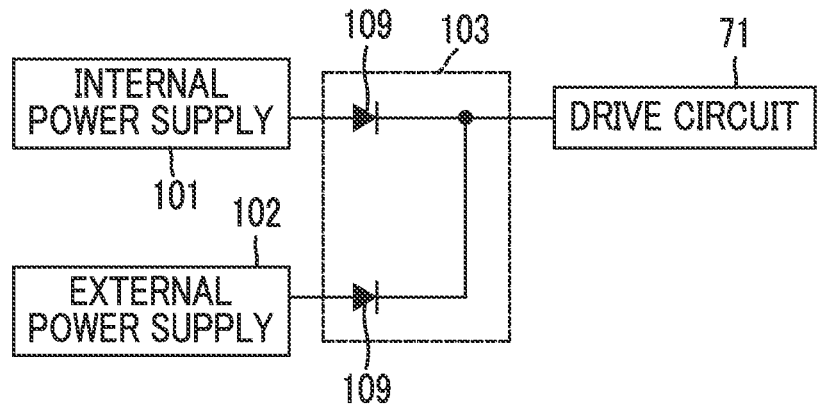
FIG. 9 shows one specific example of a circuit constituting a power feed controller.

More specifically, as shown in FIG. 9, the power feed controller 103 of the embodiment is constituted of, for example, a circuit that connects the internal power supply 101 and the external power supply 102 by a diode 109. For this reason, the power feed controller 103 performs the power feed to the drive circuit 71 using the internal power supply 101 in a case where the first voltage is greater than the second voltage. On the other hand, the power feed controller 103 performs the power feed to the drive circuit 71 using the internal power supply 101 and the external power supply 102 in a case where the first voltage output from the internal power supply 101 is smaller than the second voltage output from the external power supply 102. The power feed controller 103 can perform the power feed to the drive circuit 71 using the internal power supply 101, the external power supply 102, or the internal power supply 101 and the external power supply 102 in a case where the first voltage and the second voltage are equal.

The radiation output restriction unit 105 controls the output of the radiation by a power supply to be used in the power feed to the drive circuit 71 by the power feed controller 103. For example, the radiation output restriction unit 105 restricts the output of the radiation by controlling the current flowing to the drive circuit 71 by the external power supply 102 in a case where the power feed to the drive circuit 71 is performed using the external power supply 102. Furthermore, the radiation output restriction unit 105 can restrict the output of the radiation by restricting a range in which setting of the output of the radiation is possible. For example, an output of specific radiation is made unselectable from a menu for setting the output of the radiation. In the embodiment, the radiation output restriction unit 105 restricts the output of the radiation by restricting a range in which setting of the output of the radiation is possible.

Figure 10:
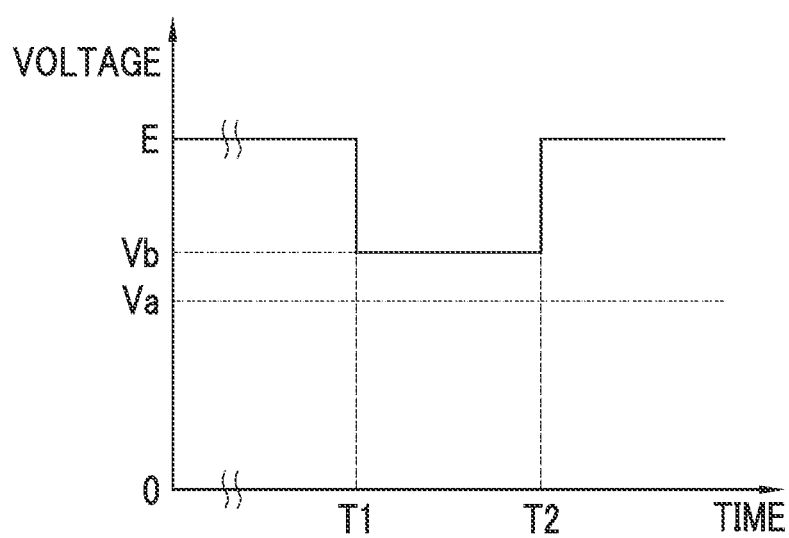
FIG. 10 is a graph showing a voltage drop of an internal power supply due to exposure of radiation.

Hereinafter, the operation in a case where radiography is performed using the radiography apparatus 10 configured as above will be described. As shown in FIG. 10, it is assumed that the electromotive force of the internal power supply 101 is "E" (V), and the second voltage that is output from the external power supply 102 is "Va" (V). Then, in a case where the exposure of the radiation is performed from a time T1 to a time T2, the first voltage that is output from the internal power supply 101 during the exposure of the radiation decreases from "E" to "Vb" (V). An output voltage (first voltage) "Vb" of the internal power supply 101 after a voltage drop can be represented by $Vb = E - R \cdot I$ using electromotive force "E", internal resistance "R" of the internal power supply 101, and consumption current "I" of the drive circuit 71.

Figure 11:
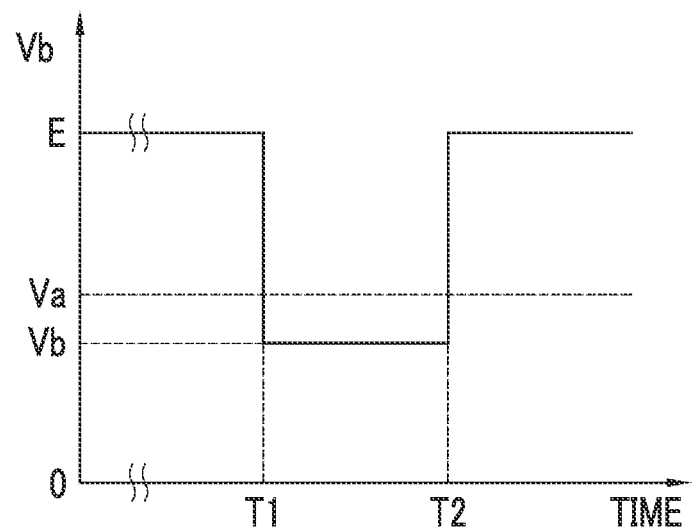
FIG. 11 is a graph showing a voltage drop of the internal power supply due to exposure of radiation.

Accordingly, as shown in FIG. 11, there is a case where the voltage (first voltage) Vb that is output from the internal power supply 101 in a case of making a current flow to the drive circuit 71 decreases less than the voltage (second voltage) Va that is output from the external power supply 102 depending on a value of the electromotive force "E" or the internal resistance "R" of the internal power supply 101 or the consumption current "I" of the drive circuit 71. In this case, the internal power supply 101 supplies a current to the drive circuit 71 within a range of the supplied electric power, and the external power supply 102 also supplies a current to the drive circuit 71. That is, in a case where Vb<Va, the external power supply 102 supplies a current corresponding to |Vb−Va| to the drive circuit 71. As a result, both the internal power supply 101 and the external power supply 102 supply electric power to the drive circuit 71.

Figure 12:
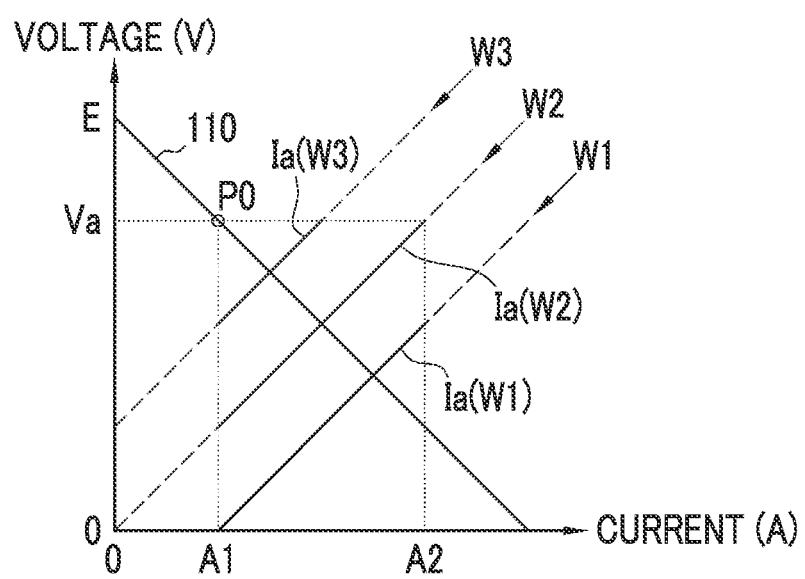
FIG. 12 is a graph showing an IV characteristic of the internal power supply and a supply limit of an external power supply.

Note that the supply capability of electric power of the external power supply 102 is finite. In a case where the external power supply 102 is a general commercial power supply in Japan, the external power supply 102 is 100 V (1500 W). For this reason, the external power supply 102 cannot endure supply of a current greater than 15 A. Accordingly, the radiation output restriction unit 105 restricts the output of the radiation within a range in which the external power supply 102 can endure. For example, as shown in FIG. 12, in a case where the radiography apparatus 10 can make a radiation output of W1 watt (for example, 2.0 kW), W2 watt (for example, 1.5 kW), and W3 watt (for example, 1.0 kW), the radiation output restriction unit 105 restricts the output of the radiation within a range indicated by a broken line not exceeding the supply capability of electric power of the external power supply 102 depending on a characteristic (an IV characteristic indicated by a graph 110) of the internal power supply 101. In FIG. 12, the radiation output of W1 watt can be set only within a range indicated by a solid line Ia (W1). Furthermore, the radiation output of W2 watt can be set only within a range indicated by a solid line Ia (W2), and the radiation output of W3 watt can be set only within a range indicated by a solid line Ia (W3). "P0" is a point where the voltage (first voltage) Vb of the internal power supply 101 during exposure and the voltage (second voltage) Va of the external power supply 102 are equal, and "A1" is a current (A) that is supplied to the drive circuit 71 by the internal power supply 101 and the external power supply 102 in this case. Furthermore, "A2" is a maximum current that can be supplied by the external power supply 102.

As described above, the radiography apparatus 10 can stably perform radiography using the internal power supply 101 and the external power supply 102. Furthermore, while the radiography apparatus 10 operates (generates the radiation) with the supply of electric power from the internal power supply 101 in principle in a case where the supply capability of electric power of the internal power supply 101 is insufficient, even though the supplied electric power from the internal power supply 101 is insufficient, the radiography apparatus 10 is not instantly made unusable, and can perform some radiography using the external power supply 102.

As described above, the voltage (first voltage) Vb that is output from the internal power supply 101 changes depending on the electromotive force "E", the internal resistance "R", and the consumption current "I" of the drive circuit 71. For this reason, it is preferable that the radiation output restriction unit 105 restricts the output of the radiation using a characteristic of the internal power supply 101. The characteristic of the internal power supply 101 is at least one of the electromotive force "E" or the internal resistance "R" of the internal power supply 101.

Figure 13:
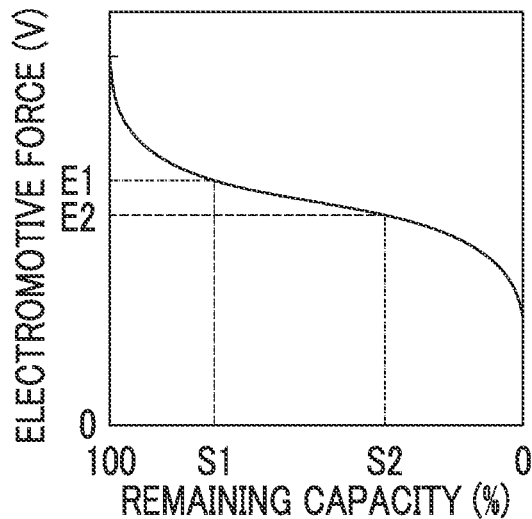
FIG. 13 is a graph showing a relationship of electromotive force and a remaining capacity of the internal power supply.

Normally, as shown in FIG. 13, the electromotive force "E" of the internal power supply 101 changes depending on a remaining capacity (%) of the internal power supply 101. For example, the electromotive force of the internal power supply 101 in a case where the remaining capacity is S1 (%) is E1 (V), and the electromotive force of the internal power supply 101 in a case where the remaining capacity is S2 (%) is E2 (V). Then, there is a case where, in a case where the electromotive force "E" of the internal power supply 101 changes, the output of the radiation needs to be further restricted. For example, in a case where the electromotive force "E" of the internal power supply 101 decreases to such a degree as to be not compensated within a range of the solid line Ia (W3), the external power supply 102 does not endure the output of the radiation of W3 watt, and thus, the radiation output restriction unit 105 needs to restrict (prohibit) the output of the radiation of W3 watt.

Figure 14:
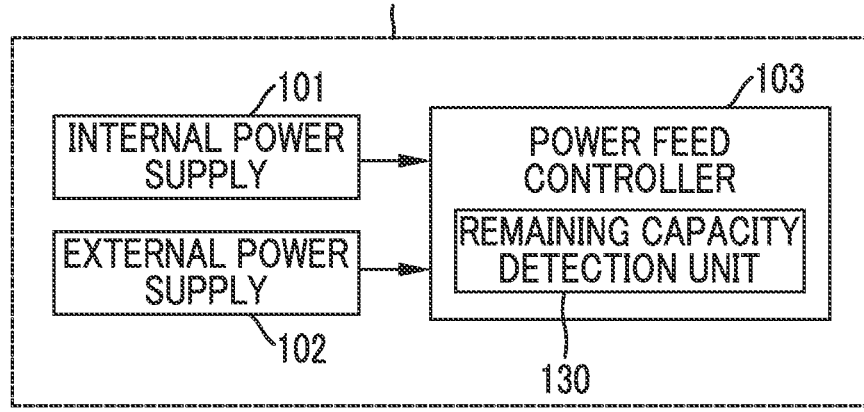
FIG. 14 is a block diagram of a power feed controller that detects the remaining capacity of the internal power supply.

For this reason, as shown in FIG. 14, it is preferable that the power feed controller 103 comprises a remaining capacity detection unit 130 that detects the remaining capacity of the internal power supply 101. In this case, the radiation output restriction unit 105 can more properly restrict the output of the radiation using the remaining capacity of the internal power supply 101 that is an output result of the remaining capacity detection unit 130. As a result, it is possible to safely continue radiography without depending on the remaining capacity of the internal power supply 101. The remaining capacity detection unit 130 is a sensor, a circuit, or the like that detects the remaining capacity of the internal power supply 101.

Figure 15:
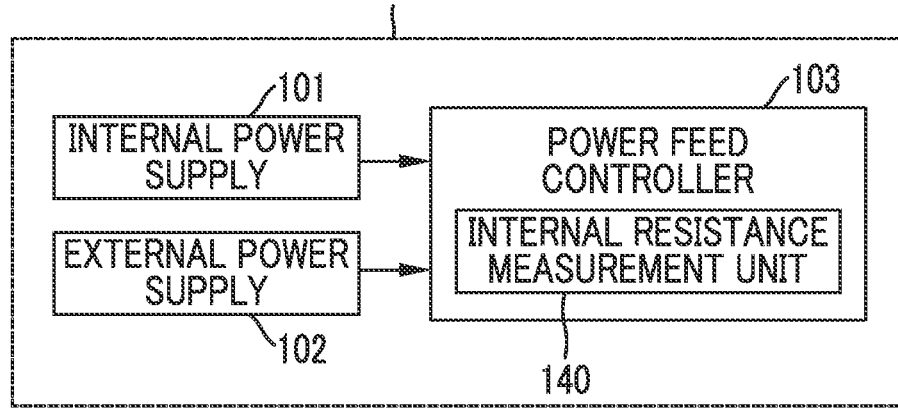
FIG. 15 is a block diagram of a power feed controller that measures internal resistance of the internal power supply.

The internal resistance "R" of the internal power supply 101 is deteriorated over time (the internal resistance "R" increases) due to repetitive use. In a case where the internal resistance "R" changes, a slope of the graph 110 in FIG. 12 changes, and thus, a range of the output of the radiation that should be restricted by the radiation output restriction unit 105 changes. For this reason, as shown in FIG. 15, it is preferable that the power feed controller 103 comprises an internal resistance measurement unit 140 that measures the internal resistance "R" of the internal power supply 101, and the radiation output restriction unit 105 more properly restricts the output of the radiation using the internal resistance "R" that is a measurement result of the internal resistance measurement unit 140. In this way, it is possible to safely continue radiography without depending on an increase in internal resistance "R", that is, deterioration over time of the internal power supply 101. The internal resistance measurement unit 140 is a sensor, a circuit, or the like that measures the internal resistance of the internal power supply 101.

The power feed controller 103 can comprise both the remaining capacity detection unit 130 and the internal resistance measurement unit 140. In this case, the radiation output restriction unit 105 can consider both the remaining capacity and the internal resistance "R" of the internal power supply 101 in restricting the output of the radiation, and thus, it is possible to more properly and safely restrict the output of the radiation.

Second Embodiment

Figure 16:
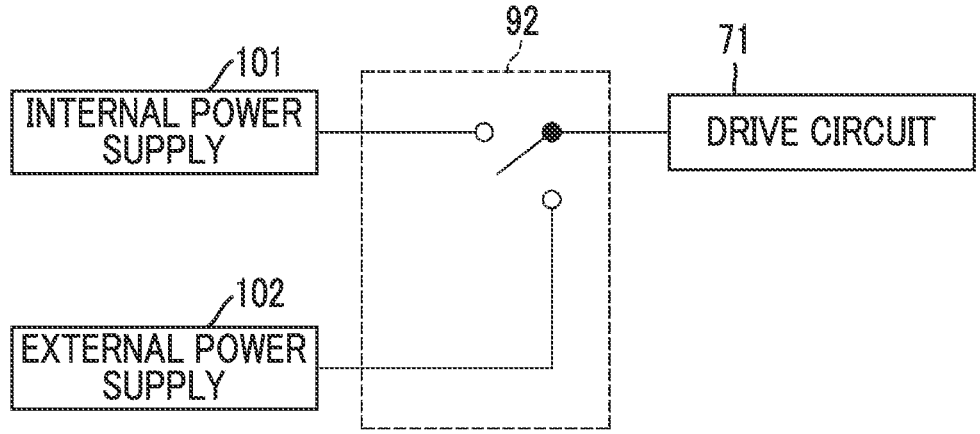
FIG. 16 shows one specific example of a circuit constituting a power feed controller of a second embodiment.

In the above-described first embodiment, although the power feed controller 103 performs the power feed to the drive circuit 71 using the internal power supply 101 and the external power supply 102, the power feed controller 103 can switch a power supply, which performs the power feed to the drive circuit 71, between the internal power supply 101 and the external power supply 102. That is, the power feed controller 103 can perform the power feed to the drive circuit 71 selectively using either the internal power supply 101 or the external power supply 102. For example, as shown in FIG. 16, the power feed controller 103 is constituted of a switching circuit that switches the power supply to be connected to the drive circuit 71 between the internal power supply 101 and the external power supply 102. Then, the radiation output restriction unit 105 restricts the output of the radiation within a range in which electric power can be supplied by the external power supply 102 in a case where the power feed controller 103 performs switching from the internal power supply 101 to the external power supply 102.

In this way, in a case of switching between the internal power supply 101 and the external power supply 102, even though the internal power supply 101 falls into an insufficient remaining capacity or the like, minimum radiography can be performed using the external power supply 102 under the control of the radiation output restriction unit 105.

As described above, in a case of switching between the internal power supply 101 and the external power supply 102, the power feed controller 103 can perform switching between the internal power supply 101 and the external power supply 102 using a threshold value to be set for the remaining capacity of the internal power supply 101, for example. This is to avoid a case where radiography cannot be normally completed due to the insufficient remaining capacity of the internal power supply 101.

Figure 17:
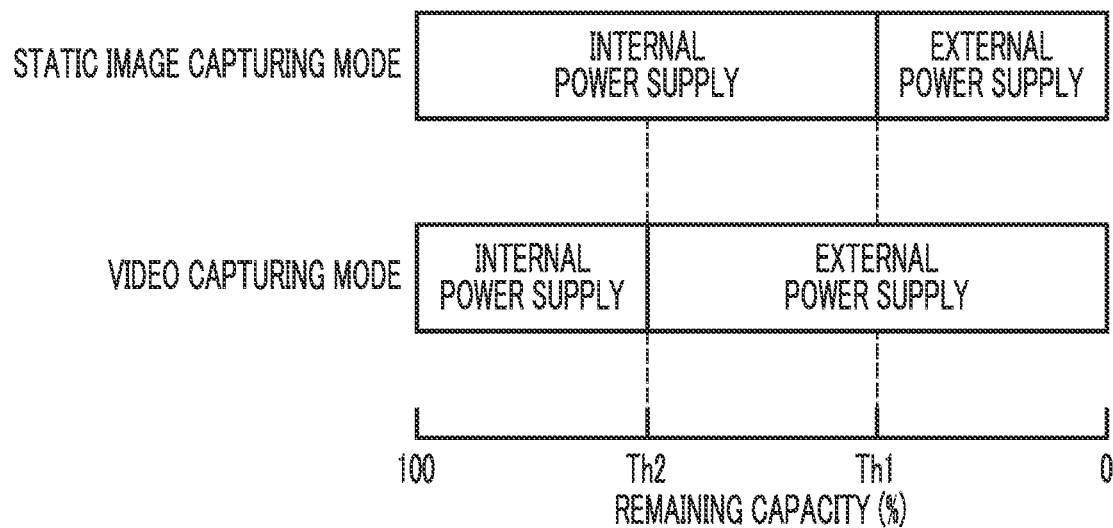
FIG. 17 is an explanatory view showing a relationship between the remaining capacity of the internal power supply and a threshold value for switching between the internal power supply and the external power supply.

As described above, in a case of switching using the threshold value to be set the remaining capacity of the internal power supply 101, it is preferable that the power feed controller 103 sets different threshold values between a static image capturing mode in which a static image is captured using radiation and a video capturing mode in which video is captured using radiation. For example, as shown in FIG. 17, a threshold value for switching between the internal power supply 101 and the external power supply 102 in the static image capturing mode is set to "Th1", and a threshold value for switching between the internal power supply 101 and the external power supply 102 in the video capturing mode is set to a threshold value Th2 greater than the threshold value Th1 in the static image capturing mode (Th2>Th1). This is to suppress the occurrence of trouble that the remaining capacity of the internal power supply 101 is insufficient in the middle of video capturing because capturing of video has a long exposure time compared to capturing a static image. Furthermore, capturing of a static image has a short exposure time compared to capturing of video, and thus, it is possible to perform radiography with no restriction by the radiation output restriction unit 105 many times effectively using the remaining capacity of the internal power supply 101 to the limit.

Figure 18:
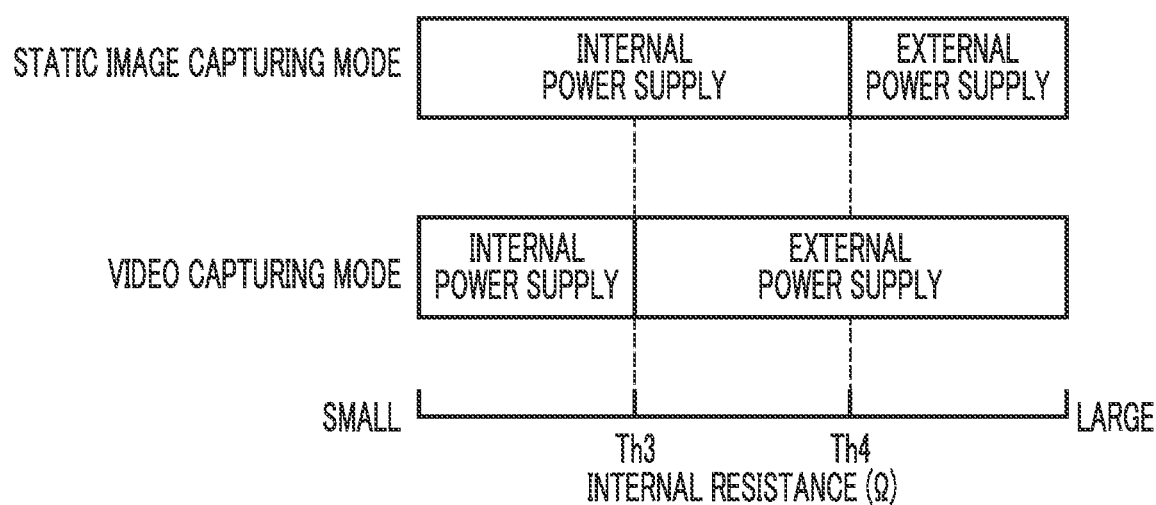
FIG. 18 is an explanatory view showing a relationship between the internal resistance of the internal power supply and the threshold value for switching between the internal power supply and the external power supply.

In the above-described second embodiment, although the power feed controller 103 sets the threshold value for the remaining capacity of the internal power supply 101, a threshold value for the internal resistance "R" of the internal power supply 101 can be set instead of or in addition to the threshold value for the remaining capacity of the internal power supply 101, and the internal power supply 101 and the external power supply 102 can be switched using the threshold value regarding the internal resistance "R". In a case where the threshold value for the internal resistance "R" is set, and the threshold value is made different between the static image capturing mode and the video capturing mode, as shown in FIG. 18, a threshold value Th3 of the static image capturing mode may be set to a value smaller than a threshold value Th4 of the video capturing mode. This is to effectively utilize electric power of the internal power supply 101 in capturing of a static image, and to suppress the occurrence of an insufficient remaining capacity in the middle of exposure in capturing of video.

In the above-described second embodiment, although the internal power supply 101 and the external power supply 102 are switched using the threshold value to be set for the remaining capacity or the like of the internal power supply 101, in regard to the threshold value to be set for the remaining capacity or the like of the internal power supply 101, it is preferable to use the threshold value having different values between a case of switching from the internal power supply 101 to the external power supply 102 and a case of switching from the external power supply 102 to the internal power supply 101. That is, it is preferable that the threshold value to be set for the remaining capacity or the like of the internal power supply 101 is given hysteresis. For example, as shown in FIGS. 19A and 19B, a threshold value ThA (FIG. 19A) for switching from the internal power supply 101 to the external power supply 102 and a threshold value ThB (FIG. 19B) for switching from the external power supply 102 to the internal power supply 101 are set to different values (ThA≠ThB). In a case where the threshold value ThA and the threshold value ThB are the threshold value to be set for the remaining capacity of the internal power supply 101, the threshold values ThA and ThB are set to be ThA<ThB (FIGS. 19A and 19B). In a case where the threshold value ThA and the threshold value ThB are the threshold value to be set for the internal resistance of the internal power supply 101, the threshold values ThA and ThB are set to be ThA>ThB (not shown). In this way, in a case where switching between the internal power supply 101 and the external power supply 102 is given hysteresis, it is possible to prevent frequent switching. As a result, it is possible to continue stable radiography.

In a case where radiation is being generated (during exposure), as shown in FIG. 20, the power feed controller 103 postpones switching of the power supply. This is to complete appropriate radiography. Note that there is an inevitable case where the remaining capacity of the internal power supply 101 is zero, or the like. For this reason, as shown in FIG. 21, it is preferable that the controller 91 comprises an exposure time calculation unit 210 and a notification unit 211. The exposure time calculation unit 210 measures a time for which electric power can be supplied to the drive circuit 71 using the internal power supply 101. Then, the notification unit 211 notifies of the time for which electric power can be supplied to the drive circuit 71 using the internal power supply 101, through display on a monitor 37, generation of sound, or the like. With this, it is possible to allow the user to recognize a time for which radiography can be performed continuously using the internal power supply 101, and as a result, to avoid imaging failure due to switching of a power supply during generation of radiation.

In the first embodiment, the second embodiment, and the like described above, although the radiography apparatus 10 has been described, in a case where a radiation generation unit 22 has an internal power supply 101, an external power supply 102, and a radiation output restriction unit 105, the radiation generation unit 22 exhibits the same effects as the radiography apparatus 10 of at least one of the first embodiment or the second embodiment. That is, the first embodiment, the second embodiment, and the like described above include a radiation generation apparatus comprising a radiation source that generates radiation, a drive circuit that drives the radiation source, an internal power supply that makes a current flow to the drive circuit at a first voltage, an external power supply that makes a current flow to the drive circuit at a second voltage different from the first voltage, a power feed controller that performs power feed to the drive circuit using at least one of the internal power supply or the external power supply, and a radiation output restriction unit that controls an output of the radiation depending on a power supply to be used in the power feed to the drive circuit by the power feed controller.

Furthermore, the first embodiment, the second embodiment, and the like described above include a method of driving a radiography apparatus (or a radiation generation apparatus) comprising a radiation source that generates radiation, a drive circuit that drives the radiation source, an internal power supply that makes a current flow to the drive circuit at a first voltage, an external power supply that makes a current flow to the drive circuit at a second voltage different from the first voltage, and a power feed controller that performs power feed to the drive circuit using at least one of the internal power supply or the external power supply, the method having, at the radiation output restriction unit, a step of controlling an output of the radiation depending on a power supply to be used in the power feed to the drive circuit by the power feed controller.

In the first embodiment and the second embodiment described above, although two kinds of power supplies of the internal power supply 101 and the external power supply 102 are provided, the invention can be applied to a radiography apparatus that comprises a first power supply and a second power supply having different profiles of at least one a voltage or a current to be output. For example, the invention can be suitably applied to a radiography apparatus and a radiation generation apparatus in which two kinds of batteries (internal power supplies) having different profiles of at least one of a voltage or a current to be output are mounted. Furthermore, the invention can be suitably applied to a radiography apparatus and a radiation generation apparatus that have three or more power supplies having different profiles of at least one of a voltage or a current to be output.

In the above-described embodiment, the hardware structures of processing units that execute various kinds of processing, such as the controller 91, the image processing unit 93, the power feed controller 103, the radiation output restriction unit 105, the exposure time calculation unit 210, and the notification unit 211, are various processors described below. Various processors include a graphical processing unit (GPU), a programmable logic device (PLD) that is a processor capable of changing a circuit configuration after manufacture, such as a field programmable gate array (FPGA), a dedicated electric circuit that is a processor having a circuit configuration dedicatedly designed for executing various kinds of processing, and the like in addition to a central processing unit (CPU) that is a general-purpose processor executing software (program) to function as various processing units.

One processing unit may be configured of one of various processors described above or may be configured of a combination of two or more processors (for example, a plurality of FPGAs, a combination of a CPU and an FPGA, or a combination of a CPU and a GPU) of the same type or different types. A plurality of processing units may be configured of one processor. As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structures of various processors are, more specifically, electric circuits (circuitry), in which circuit elements, such as semiconductor elements, are combined.

EXPLANATION OF REFERENCES

10: radiography apparatus
11: imaging unit
12: display unit
15: subject
21: imaging unit body
22: radiation generation unit
23: radiography unit
25: C-arm
27: caster
31: cable
36: display unit body
37: monitor
41: first operating unit
42: attachment and detachment detection unit
51: sliding mechanism
52: lifting mechanism
61: second operating unit
71: drive circuit
72: radiation source
73: collimator
74: irradiation range display unit
75: mono-tank
81: radiography panel
82: grid
83: battery
91: controller
92: power supply unit
93: image processing unit
101: internal power supply
102: external power supply
103: power feed controller
105: radiation output controller
109: diode
110: graph
130: remaining capacity detection unit
140: internal resistance measurement unit
210: exposure time calculation unit
211: notification unit
A1: current
A2: current
I: consumption current
E, E1, E2: electromotive force
Ia(W1): solid line
Ia(W2): solid line
Ia(W3): solid line
P0: point
T1: time
T2: time
Th1: threshold value Th2: threshold value
Th3: threshold value
Th4: threshold value
ThA: threshold value
ThB: threshold value
Va: second voltage
Vb: first voltage

What is claimed is:

1. A radiation generation apparatus comprising:
a radiation source that generates radiation;
a drive circuit that drives the radiation source;
an internal power supply that makes a current flow to the drive circuit at a first voltage;
an external power supply that makes a current flow to the drive circuit at a second voltage different from the first voltage; and
a processor configured to function as:
a power feed controller that performs power feed to the drive circuit using at least one of the internal power supply or the external power supply; and
a radiation output restriction unit that controls an output of the radiation by a power supply to be used in the power feed to the drive circuit by the power feed controller,
wherein the power feed controller switches a power supply, which performs the power feed to the drive circuit, between the internal power supply and the external power supply,
wherein the power feed controller performs switching between the internal power supply and the external power supply using a threshold value set for a remaining capacity of the internal power supply,
wherein the power feed controller sets the threshold value that is different between a case where a static image is captured using the radiation and a case where video is captured using the radiation, and
wherein the power feed controller uses the threshold value having different values between a case of switching from the internal power supply to the external power supply and a case of switching from the external power supply to the internal power supply.

2. The radiation generation apparatus according to claim 1,
wherein the power feed controller performs the power feed to the drive circuit using the internal power supply and the external power supply.

3. The radiation generation apparatus according to claim 1,
wherein the power feed controller performs the power feed to the drive circuit using the internal power supply and the external power supply in a case where the first voltage is smaller than the second voltage.

4. The radiation generation apparatus according to claim 1,
wherein the radiation output restriction unit restricts the output of the radiation using a characteristic of the internal power supply.

5. The radiation generation apparatus according to claim 4,
wherein the radiation output restriction unit restricts the output of the radiation using a remaining capacity of the internal power supply.

6. The radiation generation apparatus according to claim 5,
wherein the radiation output restriction unit restricts the output of the radiation using internal resistance of the internal power supply.

7. The radiation generation apparatus according to claim 4,
wherein the radiation output restriction unit restricts the output of the radiation by restricting the current flowing from the external power supply to the drive circuit.

8. The radiation generation apparatus according to claim 4,
wherein the radiation output restriction unit restricts the output of the radiation by restricting a range in which setting of the output of the radiation is possible.

9. A radiation generation apparatus comprising:
a radiation source that generates radiation;
a drive circuit that drives the radiation source;
an internal power supply that makes a current flow to the drive circuit at a first voltage;
an external power supply that makes a current flow to the drive circuit at a second voltage different from the first voltage; and
a processor configured to function as:
a power feed controller that performs power feed to the drive circuit using at least one of the internal power supply or the external power supply; and
a radiation output restriction unit that controls an output of the radiation by a power supply to be used in the power feed to the drive circuit by the power feed controller,
wherein the power feed controller switches a power supply, which performs the power feed to the drive circuit, between the internal power supply and the external power supply,
wherein the power feed controller performs switching between the internal power supply and the external power supply using a threshold value set for a remaining capacity of the internal power supply,
wherein the power feed controller sets the threshold value that is different between a case where a static image is captured using the radiation and a case where video is captured using the radiation,
wherein the power feed controller uses the threshold value having different values between a case of switching from the internal power supply to the external power supply and a case of switching from the external power supply to the internal power supply, and
wherein the threshold value that is set in a case where the video is captured using the radiation is greater than the threshold value that is set in a case where the static image is captured using the radiation.

10. The radiation generation apparatus according to claim 1,
wherein the power feed controller postpones the switching of the power supply while the radiation is being generated.

11. The generation apparatus according to claim 1, wherein the processor is further configured to function as:
a notification unit that notifies of a time for which the power feed to the drive circuit using the internal power supply is possible.

12. The radiation generation apparatus according to claim 1,
wherein the radiation output restriction unit restricts the output of the radiation in a case where the power feed controller performs switching from the internal power supply to the external power supply.

* * * * *